United States Patent [19]

Kurtz

[11] Patent Number: 5,037,407
[45] Date of Patent: Aug. 6, 1991

[54] ELECTRONIC MONITORING SYSTEM FOR DRAINAGE DEVICE

[75] Inventor: Robert J. Kurtz, New York, N.Y.
[73] Assignee: BioResearch, Inc., Farmingdale, N.Y.
[21] Appl. No.: 501,840
[22] Filed: Mar. 30, 1990
[51] Int. Cl.$^5$ .................... A61M 1/00; A61M 31/00
[52] U.S. Cl. ........................ 604/319; 604/65
[58] Field of Search .................... 73/3, 40, 861.41; 604/318, 320, 67, 65, 66, 35, 321, 325, 319

[56] References Cited

U.S. PATENT DOCUMENTS

| | | | |
|---|---|---|---|
| 3,390,577 | 7/1968 | Phelps et al. | 73/861.41 |
| 3,736,930 | 6/1973 | Georgi | 604/67 |
| 4,137,913 | 2/1979 | Georgi | 604/67 |
| 4,299,218 | 11/1981 | Knigge et al. | 604/67 |
| 4,504,263 | 3/1985 | Steuer et al. | 604/67 |
| 4,532,936 | 8/1985 | LeVeen | 604/67 |
| 4,617,020 | 10/1986 | Kurtz | 604/321 |
| 4,710,165 | 12/1987 | McNeil et al. | 604/67 |

Primary Examiner—Randall L. Green
Assistant Examiner—R. Clarke
Attorney, Agent, or Firm—Larson & Taylor

[57] ABSTRACT

An electronic monitoring system for a drainage device is provided with a bubble detector which transmits a signal upon the passage of a bubble through a bubble chamber of a surgical drainage device. There is provided a timing device which may be preset for any desired period of time. The timing device is connected to an alarm or signalling device which is activated to indicate the absence of passage of a bubble through the bubble chamber during the preset time interval. Switching means is provided on the timing device to selectively activate the timer initially to a short time period of a relatively few minutes and later to a long time period of several hours. The short time period is activated initially when the drainage device is first connected to a patient so that an alarm will be sounded to indicate possible malfunction of the device indicated by the absence of a bubble during a relatively short time period. During the latter stages of recovery of the patient, the timer is set to a long time period so that the alarm or signal will be activated by the absence of a bubble during the long time period to indicate that the patient has healed sufficiently to permit the drainage device to be removed.

4 Claims, 1 Drawing Sheet

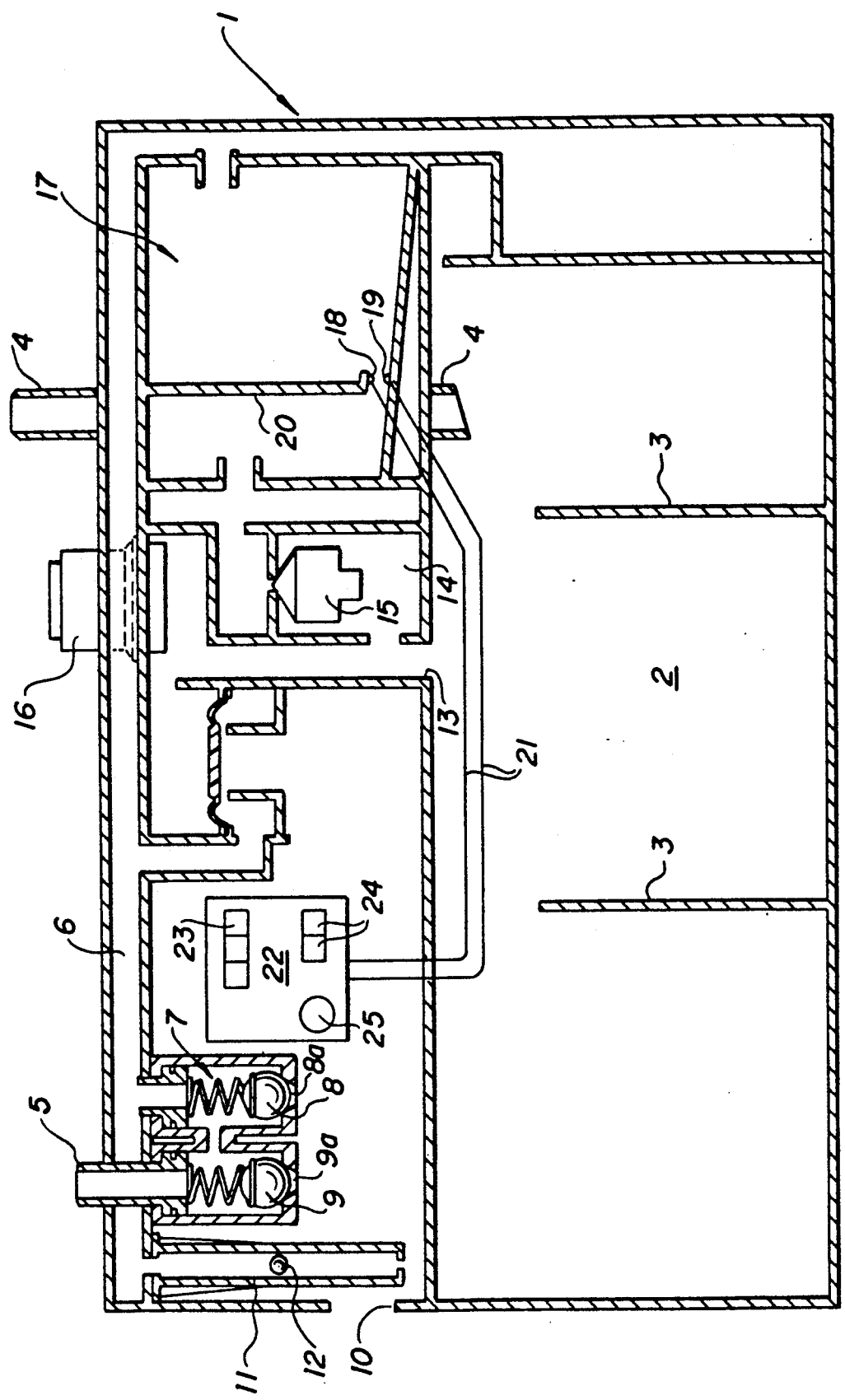

ELECTRONIC MONITORING SYSTEM FOR DRAINAGE DEVICE

FIELD OF THE INVENTION

The present invention relates to drainage devices used primarily to maintain a required degree of negativity within the patient's pleural cavity wherein a method and apparatus is provided both for determining a malfunction in the operation of the drainage device and for determining when the patient is sufficiently healed to permit removal of the drainage device.

BACKGROUND OF THE INVENTION

It is well known in the prior art to provide a drainage device which serves to maintain a required degree of negativity within the pleural cavity of a patient and to remove fluids from within the pleural cavity so that the lungs of the patient can fully expand. U.S. Pat. No. 3,363,626 issued Jan. 16, 1968 discloses the first unitary system for achieving these results. This device provides a collection chamber, an underwater seal chamber which prevents atmospheric air from entering the patient's pleural cavity and a pressure manometer chamber which maintains the degree of suction at the proper level within the collection chamber and patient's pleural cavity. During normal operation of the drainage device of the type disclosed in the above-mentioned patent, air from the patient's pleural cavity bubbles through the underwater seal chamber and out through the device through the suction outlet. The physician may observe the passage of bubbles through the underwater seal chamber but obviously this is only possible when the physician is with the patient. Thus, there is a need for providing a drainage device which will incorporate diagnostic systems which will keep hospital personnel aware of the functioning of the drainage device and the condition of the patient.

In U.S. Pat. No. 4,617,020 issued Oct. 14, 1986 there is disclosed an air leak detector and counter for a drainage device wherein bubbles are detected electronically as the bubbles pass through the underwater seal chamber and an output circuit is provided which is responsive to the signals and both counts the number of bubbles passing through the underwater seal and resets a timer at zero each time a bubble passes through the device so that the physician can, by looking at the timer, determine the time elapsed since the last bubble went through the seal chamber. It is important for the physician to know how long a time period has elapsed since a bubble went through the bubble chamber so that the physician can determine when the patient is sufficiently healed that the drainage device may be removed from connection with the pleural cavity of the patient. If, for example, the physician decides that a three hour time period without passage of a bubble is sufficient to release a patient from the hospital, the drainage device may be disconnected from the patient when the timer shows that a three hour time period elapsed since a bubble passed through the drainage device. However, it is also desirable to provide a mechanism which will ensure that the drainage device is operating properly when it is initially connected to the patient's pleural cavity. It is most important that the physician is made immediately aware of any malfunction of the drainage device in order to prevent collapse of the patient's lungs which could, of course, prove fatal. The presently disclosed invention achieves all of the foregoing objectives.

SUMMARY OF THE INVENTION

The purpose of the present invention is to provide a drainage device with an electronic detection system which will permit the physician to determine that the drainage device is operating properly when the patient is in the most critical condition when initially connected to a drainage device and to also provide means for determining when the patient has sufficiently healed so that the drainage device can be removed and the patient released from the hospital.

These objectives are achieved by providing a block timing mechanism in which time periods may be preset, one time period being relatively short, such as, for example, a matter of minutes, and the other time period being in the order of several hours. The shorter time period is utilized to ensure that the drainage device is operating properly during the initial period of recovery of the patient. For example, if the physician determines that during the first twenty-four hours of operation of the drainage device a bubble should be passing through the device at least once every five minutes, the timer is set for five minutes and so long as at least one bubble passes through the device each five minutes, the timer resets at zero and no alarm sounds. However, if no bubble passes through the drainage device within a five minute time interval, an alarm will alert hospital personnel to check the drainage device and make certain that the tubes are not plugged or that the suction line has not been inadvertently disconnected. The time interval set on the timer may be varied by the physician dependent upon the patient's condition and, towards the end of the recovery period the time interval may be set, for example, at three hours so that the physician may determine that, if no bubble passes through the drainage device during that time period, the patient's pleural cavity has healed and the drainage device may be removed.

An object of the present invention is to provide a drainage device with diagnostic means which will permit the physician to determine whether the drainage device is operating properly and when the patient has healed sufficiently to permit removal of the drainage device.

Another object of the present invention is to provide electronic bubble detector means in a drainage device which is connected to a preset block timer which resets each time a bubble passes through the drainage device during the preset time period.

Other objects and many of the attendant advantages of the present invention will become more readily apparent upon consideration of the following detailed specification in connection with the accompanying drawing wherein:

BRIEF DESCRIPTION OF THE DRAWING

The single figure of the drawing discloses a partial vertical section of a drainage device with the bubble detection system of the present invention incorporated therein.

DESCRIPTION OF THE PREFERRED EMBODIMENT

There is shown at 1 a drainage device which is generally similar to the device shown in U.S. Pat. No. 4,605,400 issued Aug. 12, 1986. There is provided a collection chamber 2 which is divided into three separate chambers by partitions 3. The inlet tube leading from the patient's pleural cavity to the collection chamber is shown at 4. The suction outlet tube from the collection chamber is shown at 5 and a passageway 6 extends across the upper end of the drainage device from the suction inlet and through suction control chambers 7. The suction control chamber 7 is provided with ball valves 8 and 9 which are spring-pressed to seat in valve seats 8a and 9a in the lower ends of suction control chamber 7. There is provided an outlet to atmosphere at 10 which communicates with the lower surfaces of ball valves 8 and 9 through the openings formed by valve seats 8a and 9a. When the suction within suction pipe 5 reaches a predetermined level of negativity, the atmospheric pressure against the lower surfaces of ball valves 8 and 9 overcomes the spring pressure and the ball valves 8 and 9 are raised to admit atmospheric air to the device to reduce the suction level within the drainage device. This general type of suction control mechanism is shown in FIG. 9 of U.S. Pat. No. 4,605,400. The suction level maintained within the drainage device is indicated by the position of a ball 12 disposed within a tube 11 which has the lower end thereof open to atmosphere.

The upper end of the collection chamber is provided with an outlet 13 which communicates with a trap chamber 14 beneath a one-way valve 15. The one-way valve permits gases to flow from the collection chamber through the one-way valve but prevents higher pressure air from passing through the valve in the reverse direction. The details of construction of this valve are disclosed in U.S. Pat. No. 4,605,400. A negative pressure relief valve 16 is mounted in the upper wall of the drainage device and this valve permits a metered amount of atmospheric air to enter the collection chamber during periods of excessive negativity within the collection chamber. The details of construction of the negative pressure relief valve are more clearly shown in FIG. 6 of U.S. Pat. No. 4,605,400.

Air passing through the one-way valve 15 passes into a bubble detection chamber 17. The details of construction and operation of the bubble detection chamber 17 are shown in FIG. 10 of U.S. Pat. No. 4,605,400 and at column 14, lines 61 - column 15, line 37. There are provided a pair of diodes 18 and 19 which are disposed across the passageway at the lower end of partition 20. When a gas bubble passes between the diodes 18 and 19, a signal is transmitted by way of transmission lines 21 to a control unit 22. The circuitry utilized in operatively connecting the bubble detection signals emitted by diodes 18 and 19 with the timer mechanism in control unit 22 is shown and described in U.S. Pat. No. 4,617,020.

The control unit 22 is provided with a time interval selector 23 so that any desired time interval varying from one minute up to six hours may be set by the time interval selector. Alternatively fixed time intervals can be preset within the control unit and operation of time interval selector 23 may be actuated to select the desired preset time interval.

A pair of switches 24 are provided one of which is actuated when the drainage device is initially connected to a patient which provides a means for ensuring that the drainage device is operating properly. For this mode of operation, a relatively short time interval is selected such as, for example, 10 to 15 minutes, so that in the event a bubble does not pass through the drainage device during the preselected time period an alarm 25 will sound together with the display of a light signal. This will alert hospital personnel to check the drainage device for blockage or other malfunction to ensure that the device is performing properly the function of maintaining a suitable level of negativity within the patient's pleural cavity. In the event a bubble passes through the bubble detector within the preset time period, the timer will automatically reset to zero.

The physician may set the time intervals for longer periods as the patient heals and ultimately the switching system 24 will be transferred to a tube removal function which provides a signal when no bubble has passed through the drainage device for a number of hours. If no bubbles are passed through the system during this period of time, an alarm will sound or alternatively a light will indicate that the patient has healed sufficiently to permit the removal of the drainage device. In the event a bubble does pass through the drainage device during the preset time interval, the timer will automatically reset to zero.

Thus, it can be seen that the present invention provides a method and apparatus for enabling a physician to determine whether or not the drainage device which has been connected with a patient's pleural cavity is in fact performing properly and further provides a system wherein the physician can determine whether the patient has healed sufficiently to permit removal of the drainage device.

Obviously many modifications and variations of the present invention are possible in light of the above teachings. What is claimed as new and is desired to be secured by Letters Patent is:

I claim:

1. A device for monitoring the operation of a drainage device for connection with the pleural cavity of a patient including a collection chamber, a bubble chamber, a passageway from the collection chamber to a cavity in the patient and a passageway from the drainage device to a suction source, means disposed adjacent the bubble chamber for detecting a bubble passing through the bubble chamber and for transmitting a bubble detection signal in response to passage of a bubble through the bubble chamber, adjustable timer means for setting predetermined time blocks for monitoring the functioning of the drainage device and condition of the patient, and means for resetting the predetermined time block to zero either upon receipt of a bubble detection signal or upon termination of the predetermined time block, signal means operatively connected with both said bubble detection means and said adjustable timer means for indicating the absence of a bubble detection signal during the predetermined time block.

2. A method of determining when to remove a drainage device from connection with the pleural cavity of a patient comprising the steps of determining a time interval without the detection of a bubble passing from the patient's pleural cavity through the drainage device required to demonstrate sufficient healing of the patient to remove the drainage device, presetting a timer to the predetermined time interval, resetting the timer to zero with each passage of a bubble through the drainage device and providing signal means operatively connected to said timer to indicate the absence of passage of bubbles through the drainage device during the predetermined time interval whereby activation of the signal means indicates that the drainage device may be removed from the patient.

3. A method for determining when a drainage device is functioning improperly when initially connected to the pleural cavity of a patient comprising the steps of determining a time interval during which at least one bubble should pass through the drainage device when the drainage device is functioning properly, presetting a timer to the predetermined time interval, resetting the timer to zero with each passage of a bubble through the drainage device, and providing signal means operatively connected to said timer to indicate the absence of passage of bubbles through the drainage device during the predetermined time interval whereby activation of the signal means indicates the drainage device is operating improperly.

4. A device for monitoring the operation of a drainage device including a collection chamber, a passageway from the collection chamber to the pleural cavity of a patient, a passageway from the drainage device to a suction source, a bubble chamber disposed in the passageway between the pleural cavity of a patient and the passageway leading to the suction source, bubble detection means disposed adjacent said bubble chamber, timer means operatively connected to said bubble detection means to receive signals therefrom indicating passage of bubbles through the bubble chamber, signal means operatively connected to said timer means, and mode selection means connected to said timer for setting in one operational mode a short time interval when the drainage device is initially connected to the pleural cavity of a patient to sound an alarm in the event no bubbling occurs during the short time interval to indicate the drainage device is not operating properly and for setting in another operational mode a relatively long time interval to sound an alarm in the event no bubbling occurs during the relatively long time interval to indicate the patient has healed sufficiently to disconnect the drainage device.

* * * * *